(12) United States Patent
Viola et al.

(10) Patent No.: US 12,370,092 B2
(45) Date of Patent: Jul. 29, 2025

(54) PLANT AND PROCESS FOR PRODUCING PULL-UP DIAPERS

(71) Applicant: M.D. VIOLA MACCHINE S.R.L., Valle Salimbene (IT)

(72) Inventors: Davide Viola, Valle Salimbene (IT); Marco Viola, Valle Salimbene (IT); Andrea Viola, Valle Salimbene (IT)

(73) Assignee: M.D. VIOLA MACCHINE S.R.L., Valle Salimbene (IT)

( * ) Notice: Subject to any disclaimer, the term of this patent is extended or adjusted under 35 U.S.C. 154(b) by 142 days.

(21) Appl. No.: 18/275,819

(22) PCT Filed: Feb. 23, 2022

(86) PCT No.: PCT/IB2022/051566
§ 371 (c)(1),
(2) Date: Aug. 4, 2023

(87) PCT Pub. No.: WO2022/185146
PCT Pub. Date: Sep. 9, 2022

(65) Prior Publication Data
US 2024/0091071 A1    Mar. 21, 2024

(30) Foreign Application Priority Data
Mar. 2, 2021   (IT) .................. 102021000004832

(51) Int. Cl.
*A61F 13/15*   (2006.01)
(52) U.S. Cl.
CPC .. *A61F 13/15804* (2013.01); *A61F 13/15699* (2013.01); *A61F 13/15723* (2013.01)
(58) Field of Classification Search
None
See application file for complete search history.

(56) References Cited

U.S. PATENT DOCUMENTS

| | | | |
|---|---|---|---|
| 8,128,771 B2* | 3/2012 | Endo ................. | A61F 13/15804 156/496 |
| 8,663,415 B2* | 3/2014 | Thorson ............ | A61F 13/15739 604/385.24 |

(Continued)

FOREIGN PATENT DOCUMENTS

| EP | 2 886 089 A1 | 6/2015 |
|---|---|---|
| EP | 3 067 204 A1 | 9/2016 |
| WO | 98/27905 A1 | 7/1998 |

OTHER PUBLICATIONS

Jun. 2, 2022 International Search Report issued in International Patent Application No. PCT/IB2022/051566.

(Continued)

*Primary Examiner* — Barbara J Musser
(74) *Attorney, Agent, or Firm* — Oliff PLC

(57) ABSTRACT

A process for producing pull-up diapers including: feeding a composite elastic web along a path; cutting out openings for the legs in an intermediate portion of the composite elastic web while the composite elastic web advances, so as to substantially cancel the supply percentage elastic elongation in a central band of an elastic element of such web; applying absorbing inserts on the intermediate portion of the composite elastic web and between successive openings for the previously cut-out legs, so as to define a series of precursors of pull-up diapers, wherein the intermediate portion of the composite elastic web corresponds to crotches of the pull-up diapers, each provided with the absorbing insert, and two opposite lateral longitudinal portions of the composite elastic web correspond to the waistbands of the pull-up diapers and wherein transverse separation zones separate one precursor from the next.

13 Claims, 6 Drawing Sheets

(56) References Cited

U.S. PATENT DOCUMENTS

2018/0057304 A1\* 3/2018 Fritz ................... B65H 63/024
2018/0168887 A1\* 6/2018 LaVon .............. A61F 13/49061

OTHER PUBLICATIONS

Jun. 2, 2022 Written Opinion issued in International Patent Application No. PCT/IB2022/051566.

\* cited by examiner

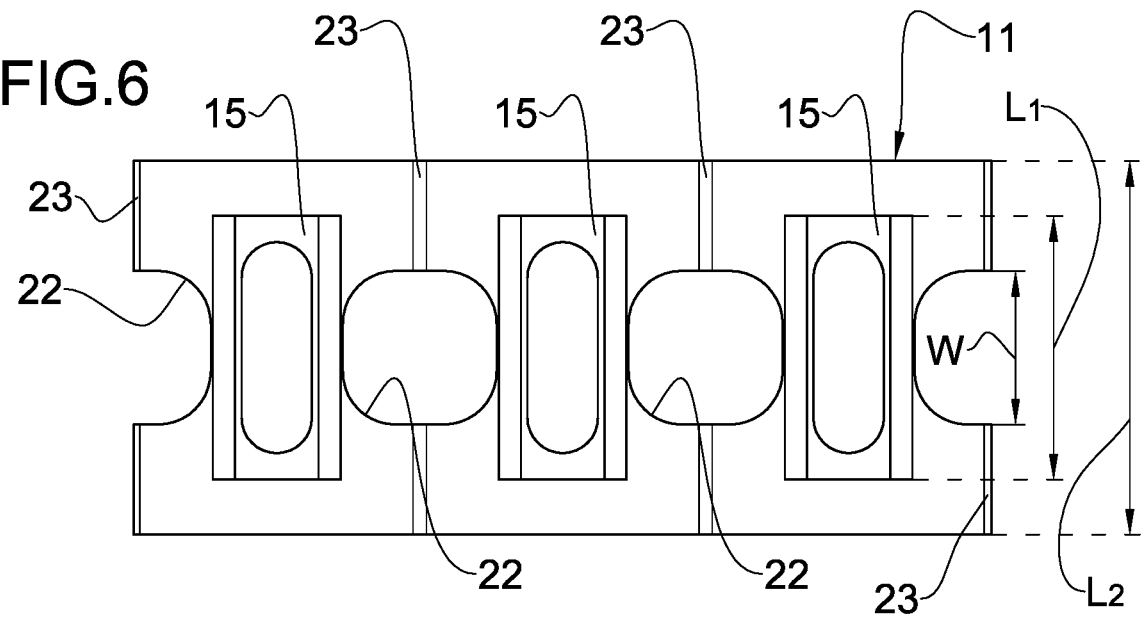
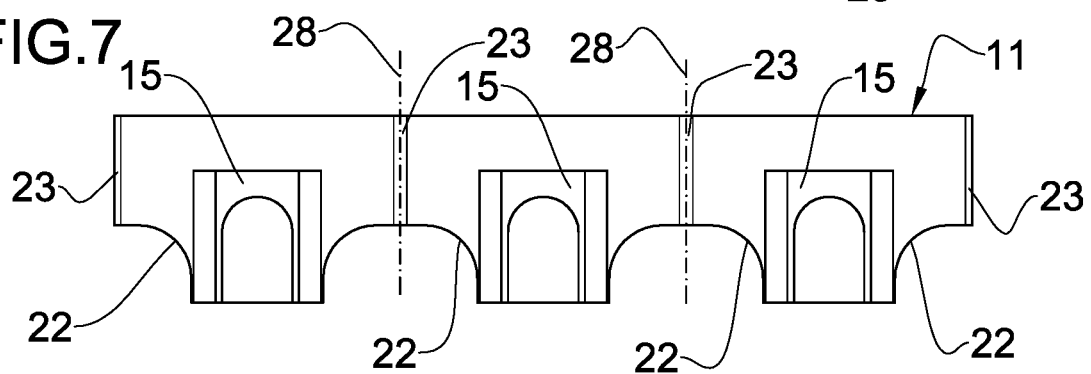
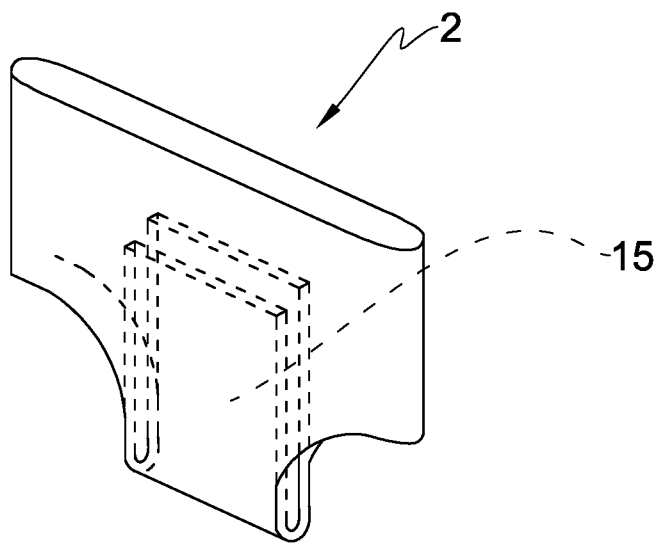

PLANT AND PROCESS FOR PRODUCING PULL-UP DIAPERS

FIELD OF THE INVENTION

The object of the present invention is a plant and a process for producing said pull-up diapers and a diaper thus obtained.

The present invention is situated in the field of production of pull-up diapers, whose packaging is executed starting from various semifinished products, including webs of material wound in reels, such as for example polyethylene, fabric, nonwoven fabric, tissue.

By pull-up diapers it is intended, in the present description and in the enclosed claims, diapers for children and for adults made in closed pull-up underwear style and also underwear and panties with appearance more similar to normal underwear and panties but provided with absorbing insert.

STATE OF THE ART

Diapers for children and adults made in closed pull-up underwear style are already known and present on the market. Such diapers are generally composed of an absorbing insert placed internally and by an external elasticized chassis that forms the pull-up. The absorbing insert has the function of absorbing the liquids and containing the solid parts. The elasticized chassis substantially has the shape of an underwear garment and has the function of supporting and adhering the absorbing insert to the body, with the object of rendering it as adherent and comfortable as possible once put on.

The manufacturing of the pull-up diapers occurs automatically and continuously in only one production line. In such line, webs of materials are unwound from the reels in order to be subsequently fed to processing stations which provide for coupling them to each other and possible to other materials, in order to form a semifinished product constituted by a composite web.

The absorbing insert is usually formed by a lower impermeable layer, an upper permeable layer and by a ground cellulose pulp mixed with absorbent powder and placed between the lower and upper impermeable layers.

The elasticized chassis is usually formed by two non-fabrics, upper and lower, and by elastic threads glued-welded in between the two non-fabrics. The two non-fabrics in the form of webs are unwound from reels and fed, maintaining them at a constant tension and the elastic threads are fixed between the two non-fabrics while they are elongated with a specific elongation, which can arrive even up to 400% of the initial length, in order to obtain an elastic web.

Such elongation/tension is maintained also during the subsequent coupling with the absorbing inserts. The composite and elastic web thus obtained is subsequently shaped, to obtain a series of open diapers, provided with the absorbing inserts and joined to each other. In particular, after the application of the absorbing inserts, the operation of leg-opening is executed, i.e. the passages for the legs are formed, by cutting them out.

The composite web is then folded longitudinally in two and welded at welding zones interposed between one diaper and the next, so as to obtain a series of closed diapers that are joined together. The abovementioned composite web is thus cut at the welding zones, so as to obtain the individual diapers. These operations are carried out while the composite web advances with continuity along a path for feeding a plant for the production of the abovementioned diapers.

When the pull-up diapers are separated and each single diaper is expelled from the plant and is no longer maintained under tension, the elastic threads tend to be contracted, i.e. they tend to return to their natural length (to the length that they have if they are not placed under tension). The contraction of the elastic threads causes the contraction of the entire diaper also in the zone of the absorbing insert. Such contraction in the zone of the absorbing insert generates folds in the absorbing insert itself and such folds can negatively affect the comfort for the person who wears the diaper and also the functionality of said diaper.

In order to overcome this problem, it is known to deactivate the elastic threads in the zone of the absorbing insert. For example, provision is made for cutting, with multiple micro-cuts, the entire zone to be deactivated, such that only that zone of the chassis, which corresponds to the absorbing insert, is without elastics under tension. For example, the public document U.S. Pat. No. 8,440,043 illustrates a method and an apparatus for deactivating elastics in a continuous elastic laminate comprising said elastics glued between a first and a second continuous substrate. The method provides for moving the elastic laminate between a cutting roller and a counter-roller, in which the cutting roller comprises a flexible blade which is bent when it comes into contact with the elastic laminate supported by the counter-roller and then elastically returns to a non-deformed configuration thereof. When the blade is bent, it exerts a pressure on the elastic laminate and cuts the elastics.

Also known is the public document EP 2 886 089 A1 which illustrates a method and an apparatus for producing diapers. According to such method and apparatus, the elastic threads are only arranged at the sides of the diapers, i.e. in different positions with respect to where the passages for the legs are made and with respect to where the absorbing inserts are applied, so that the elastic threads are not cut when the passages for the legs are made.

The public document EP 3 067 204 A1 illustrates a method for producing an elastic laminate used for making diapers, in which elastic elements are interposed between two sheets and joined to such sheets while they are moved so as to form curved trajectories. Passages for the legs are then attained in the two sheets and between the two elastic elements, i.e. without cutting said elastic elements.

In the document WO 98/27905, which also illustrates a method for making absorbing articles, the cuts for the legs are attained on the opposite longitudinal edges of the web that forms the external cover of the articles, and elastic threads are not present at edges.

OBJECT OF THE INVENTION

The Applicant has observed that the deactivation of the elastic threads operated according to the known methods is not technically easy to obtain in the correct manner. Indeed, the cutting of the elastic threads, if the cutting devices are not well-calibrated, might not be correctly executed, leaving several threads intact, or it can lead to the breakage of the entire diaper.

The Applicant has observed that, if also the deactivation is correctly executed, the diaper produced has micro-cuts in the surface fabrics and such micro-cuts, which in addition to being anti-aesthetic can still compromise the integrity of the diaper.

In addition, the need to make micro-cuts does not allow using all the types of fabric or nonwoven fabric that one would like and/or it limits the freedom to make the chassis in the desired materials and with the desired structures.

In such context, the Applicant has therefore set the objective of proposing a plant and a process for producing pull-up diapers which first of all allow making pull-up diapers of higher quality, having higher aesthetic and qualitative value than those pre-existing.

In such context, the Applicant has in particular set the objective of proposing a plant and a process which allow preventing the annoying wrinkles of the absorbing inserts themselves and simultaneously maintaining the integrity of the entire diaper.

The Applicant has in particular set the objective of proposing a plant and a process which allow preventing the wrinkles of the absorbing inserts without having to deactivate, i.e. cut, the elastic threads as in the above-illustrated prior art.

Definitions

"nominal maximum elongation of the composite elastic web": elongation beyond which the composite elastic web break or damaged or is plastically deformed; "nominal width of a pull-up diaper": maximum width obtained by laterally pulling a finished diaper so as to completely extend it; the nominal maximum elongation of the composite elastic web corresponds to the nominal width of the diapers; "percentage elastic elongation of the elastic element": percentage elastic elongation with respect to a rest length of said elastic element.

SUMMARY OF THE INVENTION

The Applicant has found that such objectives and further objects can be obtained by means of a process and a plant in accordance with the present invention, of the type claimed in the enclosed claims and/or described in the following aspects.

In particular, the Applicant has found that such objectives and further objects can be obtained by applying the absorbing inserts to the composite and elastic web (while such elastic web continues to advance along the respective path) after having formed, in the composite elastic web, the openings for the legs, so as to substantially cancel the tension and the percentage elastic elongation at the intermediate portion of the composite elastic web intended to receive the absorbing inserts. In other words, a leg-opening unit is positioned before the application of the absorbing insert, so as to release the elastics so that they are no longer retained by the portion of nonwoven fabric and elastics which is cut away.

In particular, in accordance with a first aspect, the present invention relates to a process for producing pull-up diapers, comprising:

producing a composite elastic web comprising at least one web of material and at least one elastic element longitudinally coupled to said at least one web of material;

feeding the composite elastic web along a feeding path and according to a feeding direction by giving said composite elastic web at least one supply tension such that said at least one elastic element has at least one corresponding supply percentage elastic elongation;

cutting openings for the legs in an intermediate portion of the composite elastic web while the composite elastic web advances;

applying absorbing inserts on the intermediate portion of the composite elastic web and between successive openings for the previously cut-out legs while the composite elastic web advances, so as to define a series of precursors of pull-up diapers, in which the intermediate portion of the composite elastic web corresponds a crotches of the pull-up diapers, each provided with absorbing insert, and two opposite lateral longitudinal portions of the composite elastic web correspond to the waistbands of the pull-up diapers and in which transverse separation zones separate one precursor from the next;

longitudinally folding the composite elastic web so as to bring together opposite flaps of each transverse separation zone and joining together said opposite flaps;

cutting the composite elastic web at the transverse separation zones in order to obtain the single pull-up diapers;

wherein cutting the openings for the legs involves substantially canceling the supply percentage elastic elongation in a central band of the elastic element corresponding to the intermediate portion of the composite elastic web.

In accordance with a second aspect, the present invention relates to a plant for producing pull-up diapers, comprising: a unit for feeding a composite elastic web; a leg-opening unit; an applicator; a folding device; a joining device; a cutting device. The feeding unit, the leg-opening unit, the applicator, the folding device, the joining device and the cutting device delimit a feeding path and an advancing direction of the composite elastic web. The composite elastic web comprises at least one web of material and at least one elastic element longitudinally coupled to said at least one web of material.

The leg-opening unit is placed along said feeding path and operates downstream of the feeding unit.

The applicator is placed along said feeding path, it operates downstream of the leg-opening unit and is configured for applying, on the intermediate portion of the composite elastic web and between successive openings for the previously cut-out legs, a plurality of absorbing inserts, so as to define a series of precursors of pull-up diapers, in which transverse separation zones separate one precursor from the next.

The folding device is placed downstream applicator and is configured for longitudinally folding the composite elastic web and for bringing together opposite flaps of each transverse separation zone.

The joining device is placed downstream of the folding device and is configured for joining together said opposite flaps.

The cutting device is placed downstream of the joining device and is configured for cutting the elastic web at the transverse separation zones and obtaining the single pull-up diapers.

The leg-opening unit is configured for cutting out, in an intermediate portion of the composite elastic web, openings for the legs and substantially canceling the supply percentage elastic elongation in the central band of the elastic element corresponding to the intermediate portion of the composite elastic web.

Cutting out the openings for the legs involves cutting the elastic element and this determines the substantial supply elastic percentage cancelation in the central band of the elastic element corresponding to the intermediate portion of the composite elastic web.

Optionally, the plant according to the present invention is configured for executing the process of the present invention and/or the process according to the present invention is executed by the plant of the present invention.

In a third aspect, the present invention relates to a pull-up diaper obtained by means of the process and/or with the plant of the present invention.

The Applicant has verified that the solution according to the invention first of all allows improving the quality of the pull-up diapers produced and/or making them similar or identical to a normal underwear garment.

The Applicant has in particular verified that the solution according to the invention allows producing pull-up diapers with absorbing inserts that are substantially extended, i.e. they do not have annoying wrinkles/folds. Indeed, the execution of the cuts in order to form the openings for the legs before the application of the absorbing inserts and/or the placement of the leg-opening unit upstream of the applicator allows/allow canceling the tension/elongation where the absorbing inserts are applied, since the cutting cuts a central portion of said at least one elastic element. This signifies that, once the single diapers are separated, the elastic return into the zone of the absorbing insert is substantially absent and this prevents the formation of wrinkles and irregularities.

The Applicant has also verified that the solution according to the invention allows producing pull-up diapers with integral chassis, i.e. without micro-cuts.

The Applicant has also verified that the solution according to the invention allows using different types of fabrics or nonwoven fabrics and also of structures for the elastic chassis, since such materials do not have to be cut in order to produce the micro-cuts.

Further aspects of the invention are described hereinbelow.

In one aspect, the composite elastic web comprises a first web of material, a second web of material and said at least one elastic element arranged longitudinally between the first web of material and the second web of material.

In one aspect, said at least one element of said composite elastic web comprises the or is defined by the plurality of elastic threads.

In one aspect, said at least one elastic element of said composite elastic web comprises at least one elasticized fabric or nonwoven fabric, optionally a plurality of elasticized fabrics or nonwoven fabrics, optionally arranged layered.

In one aspect, said at least one elastic element is extended substantially over the entire width of the composite elastic web.

In one aspect, the supply percentage elastic elongation is substantially canceled only in the central band of the elastic element.

In one aspect, a width of the central band and/or a maximum width of each opening for the legs is less than or substantially equal to a length of an absorbing insert.

In one aspect, a width of the central band and/or a maximum width of each opening for the legs is comprised between 50% and 100% of a length of an absorbing insert.

In one aspect, a width of the central band and/or a maximum width of each opening for the legs is comprised between 40% and 70% of a width of the composite elastic web.

The length of the absorbing insert is measured transversely with respect to a main extension direction of the composite elastic web which coincides with the feeding direction.

In one aspect, the absorbing insert is asymmetric or it is arranged asymmetrically with respect to a middle line of the composite elastic web.

In one aspect, the central band and/or the openings for the legs is/are asymmetric and positioned asymmetrically with respect to a middle line of the composite elastic web.

In one aspect, the composite elastic web has a maximum nominal elongation corresponding to a nominal width of the pull-up diapers to be produced; in which, when the composite elastic web is at its maximum nominal elongation, said at least one web of material is completely extended and said at least one elastic element has a first percentage elastic elongation.

In one aspect, the first percentage elastic elongation is substantially equal to the maximum elongation of said at least one elastic element before the elastic element breaks or in any case loses the full elastic return capacity.

In one aspect, the composite elastic web is always maintained at a substantially constant supply tension along the advancing path (before and after having applied the absorbing inserts); optionally said constant supply tension being such that the composite elastic web has an elongation equal to the maximum nominal elongation thereof.

In one aspect, before applying the absorbing inserts, provision is made for conferring to the composite elastic web a reduced tension, such that the composite elastic web has an elongation less than its maximum nominal elongation and said at least one elastic element has a second percentage elastic elongation less than the first percentage elastic elongation.

In one aspect, a ratio between the second percentage elastic elongation and the first percentage elastic elongation is less than 0.99, optionally less than 0.7.

In one aspect, a ratio between the second percentage elastic elongation and the first percentage elastic elongation is greater than 0.3, optionally greater than 0.5.

In one aspect, the first percentage elastic elongation is comprised between 200% and 600%, optionally between 300% and 500%, of a rest length.

In one aspect, the second percentage elastic elongation is comprised between 100% and 300%, optionally between 150% and 250%, of a rest length.

In one aspect, a first supply tension is comprised between 1 Kg and 5 Kg per meter of width of the web, optionally between 2 Kg and 4 Kg per meter of width.

In one aspect, the reduced tension is comprised between 0.2 Kg and 1 Kg per 100 mm of width of elastic front, i.e. of the elasticized part of the composite elastic web, optionally between 0.4 Kg and 0.8 Kg per 100 mm of width.

In one aspect, the composite elastic web comprises a first web of material, a second web of material and a plurality of elastic threads arranged longitudinally between the first web of material and the second web of material.

In one aspect, said at least one elastic element of the composite elastic web comprises the, or is defined by the, plurality of elastic threads.

In one aspect, cutting out the openings for the legs involves cutting the elastic threads arranged in the central band, leaving intact the elastic threads arranged in the two opposite lateral longitudinal portions of the composite elastic web.

In one aspect, cutting out the openings for the legs comprises removing portions of the composite elastic web from said composite elastic web.

In one aspect, producing the composite elastic web comprises: feeding the first web of material and the second web of material along respective paths; feeding said at least one elastic element, optionally the plurality of elastic threads, along a respective path; inserting said at least one elastic element between the first web of material and the second web of material and joining said at least one elastic element to the first web of material and to the second web of material while the first web of material, the second web of material and said at least one elastic element advance along a common path, in order to form the composite elastic web.

In one aspect, said at least one elastic element, preferably the plurality of elastic threads, is/are joined to the first web of material and to the second web of material by means of hot glue or ultrasound welding.

In one aspect, the elastic threads are parallel to each other.

In one aspect, the elastic threads are arranged over the entire width of the first web of material and of the second web of material.

In one aspect, during joining, said at least one elastic element, preferably the elastic threads, are given the first percentage elastic elongation.

In one aspect, during joining, the first web of material and the second web of material are completely extended.

In one aspect, during joining, a first supply tension is given to the first web of material and to the second web of material.

In one aspect, said reduced tension is conferred before having cut out the openings for the legs.

In one aspect, said reduced tension is conferred after having cut out the openings for the legs.

In one aspect, after having cut out the openings for the legs, the second percentage elastic elongation belongs to the two opposite lateral longitudinal portions of the composite elastic web.

In one aspect, the leg-opening unit is of rotary type.

In one aspect, the leg-opening unit comprises a roller provided with at least one knife and a counter-roller or counter-knife, in which the leg-opening unit cuts out, in the intermediate portion of the composite elastic web, the openings for the legs while said composite elastic web passes between the roller and the counter-roller.

In one aspect, the knife is arranged on a cylindrical lateral surface of the roller.

In one aspect, the knife has a shape corresponding to a shape of the openings for the legs.

In one aspect, a blade of the knife is extended on the cylindrical lateral surface of the roller according to a closed path.

In one aspect, the blade has a pointed form with an angle comprised between 50° and 120°.

In one aspect, a cutting point of the blade has a width comprised between 0.01 mm and 0.025 mm.

In one aspect, the roller comprises a plurality of knives arranged in succession along a circumferential direction and with a predefined pitch on the cylindrical lateral surface of the roller.

In one aspect, the leg-opening unit comprises a suction mouth placed downstream (with respect to the direction for feeding the composite elastic web) of the roller and of the counter-roller and operatively connected to suction devices, in which the suction mouth is configured for removing and moving away the portion of the composite elastic web that was cut out by the knife.

In one aspect, the roller has holes arranged on the external cylindrical surface and at the knife, in which the holes are in fluid communication with suction and blowing devices and are configured for retaining the portion of the composite elastic web just cut out by the knife on the roller and releasing it towards the suction mouth.

In one aspect, the roller or at least one cylindrical lateral surface of the roller is made of K110 steel or of tungsten carbide.

In one aspect, the blade of the knife is made on the roller by means of removing material from the cylindrical lateral surface of the roller.

In one aspect, the counter-roller or counter-knife or at least one cylindrical lateral surface of the counter-roller is made of K110 steel or of tungsten carbide.

In one aspect, a cylindrical lateral surface of the counter-roller is smooth and/or ground.

In one aspect, the roller is placed above the counter-roller.

In one aspect, springs are provided which are operatively coupled to the roller in order to maintain it lifted by the counter-roller and cancel or partly compensate for the weight of the roller.

In one aspect, the leg-opening unit comprises adjustment devices, optionally pneumatic cylinders, configured for adjusting a pressure exerted by the roller and by the knife on the counter-roller.

In one aspect, the plant also comprises at least one motorized surface, optionally at least one pair of opposite motorized surfaces, configured for engaging and advancing the composite elastic web according to the advancing direction.

In one aspect, the plant also comprises a control unit operatively connected to said at least one motorized surface and configured and/or programmed for adjusting a linear speed of said at least one motorized surface such to: give to the composite elastic web a reduced tension such that the composite elastic web has an elongation less than its maximum nominal elongation and said at least one elastic element has a second percentage elastic elongation less than the first percentage elastic elongation at least when the composite elastic web is placed downstream of said at least one motorized surface and at the applicator.

In one aspect, said at least one motorized surface is placed upstream of the leg-opening unit.

In one aspect, said at least one motorized surface is placed downstream of the leg-opening unit.

In one aspect, the control unit is configured and/or programmed for advancing the composite elastic web at the reduced speed in an application zone of the applicator and while the applicator applies the absorbing inserts on the elastic web.

In one aspect, the applicator comprises a transport surface configured for retaining the absorbing inserts and transporting them one after the other into an application zone.

In one aspect, in said application zone, the transport surface faces and is close to the composite elastic web so as to abut the absorbing insert against the composite elastic web and release the absorbing insert on the composite elastic web.

In one aspect, the control unit is operatively connected to the applicator and is configured and/or programmed for adjusting a linear speed of the transport surface.

In one aspect, said linear speed of the transport surface is, at least in the application zone, substantially equal to the reduced speed of the composite elastic web.

In one aspect, the applicator comprises a rotatable wheel and the transport surface is a peripheral surface of said rotatable wheel.

In one aspect, the absorbing inserts are glued on the composite elastic web.

In one aspect, the applicator comprises a dispenser of hot glue, optionally of spray type, operatively active at the application zone or immediately upstream of the same, in order to dispense said hot glue on the composite elastic web and/or on the absorbing insert before applying said absorbing insert to said composite elastic web.

In one aspect, the rotatable wheel comprises suction devices operatively active on the peripheral surface in order to retain the absorbing inserts and in order to release them one at a time on the composite elastic web.

In one aspect, the feeding unit of the composite elastic web comprises: devices for feeding a first web of material and a second web of material along respective paths; devices for feeding said at least one elastic element, preferably a plurality of elastic threads, along a respective path; a coupling device configured for inserting said at least one elastic element, preferably the plurality of elastic threads, between the first web of material and the second web of material and joining said at least one elastic element, preferably the plurality of elastic threads, to the first web of material and to the second web of material.

In one aspect, the leg-opening unit is configured for cutting out, in an intermediate portion of the composite elastic web, openings for the legs and cutting the elastic threads arranged in a central band of the composite elastic web, leaving intact the elastic threads arranged in two opposite lateral longitudinal portions of the composite elastic web.

In one aspect, the control unit is operatively connected to the devices for feeding the first web of material and the second web of material, to the devices for feeding said at least one elastic element, preferably of the plurality of elastic threads, and to the coupling device and is configured and/or programmed to join the first web of material, the second web of material and said at least one elastic element, preferably the plurality of elastic threads, giving to said at least one elastic element, preferably to the elastic threads, the first percentage elastic elongation and giving to the first web of material and to the second web of material the first tension and/or while the first web of material and the second web of material are completely extended.

In one aspect, the coupling device is configured for arranging the elastic threads parallel to each other.

In one aspect, the coupling device is configured for arranging said at least one elastic element, preferably the elastic threads, for the entire width of the first web of material and of the second web of material.

In one aspect, the coupling device comprises a pair of opposite coupling rollers, optionally motorized.

In one aspect, the control unit is configured and/or programmed for giving to the pair of opposite coupling rollers of the coupling device a peripheral speed greater than the application linear speed of said at least one motorized surface.

In one aspect, the coupling device comprises a hot glue dispenser or an ultrasound welder operatively active at the pair of coupling rollers.

In one aspect, the composite elastic web is previously produced in a different place and/or with a different apparatus/device and then wound in a reel.

In one aspect, a reel holder is configured to carry, in a reel, the composite elastic web and provision is made for feeding the composite elastic web along said path and according to said advancing direction by unwinding from the reel holder.

In one aspect, said at least one motorized surface, optionally the first motorized surface and the second motorized surface, is/are placed downstream of the reel holder in order to engage and advance the composite elastic web unwound from the reel holder.

Further characteristics and advantages will be clearer from the detailed description of a preferred but not exclusive embodiment of a plant and a process for producing pull-up diapers in accordance with the present invention.

BRIEF DESCRIPTION OF THE DRAWINGS

Such description will be set forth hereinbelow with reference to the enclosed drawings, provided only as a non-limiting example, in which:

FIGS. 5-7 illustrate a composite elastic web for making pull-up diapers in respective processing steps in the plant of FIG. 1; and FIG. 8 illustrates a pull-up diaper attained according to the invention.

DETAILED DESCRIPTION OF PREFERRED EMBODIMENTS OF THE INVENTION

Figure 1:
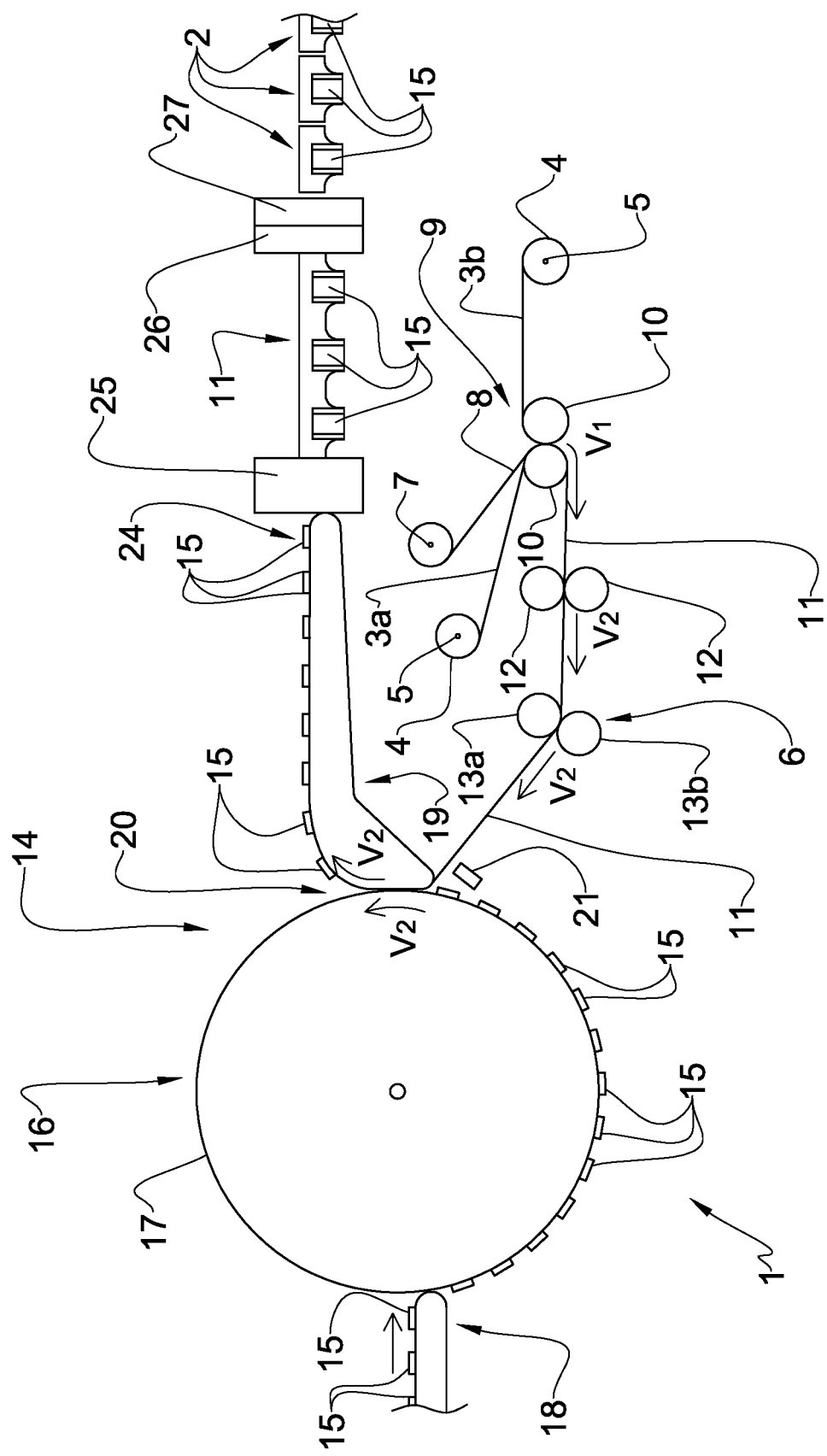
FIG. 1 shows a side elevation schematic view of a plant for producing pull-up diapers according to the present invention.

With reference to the enclosed figures, reference number 1 overall indicates a manufacturing plant for producing pull-up diapers 2. All the steps/operations described hereinbelow are executed in a continuous manner, without interruptions on a single production line of the plant 1 in accordance with the process according to the present invention.

In the plant 1, the packaging of the abovementioned pull-up diapers 2 is executed starting from different semi-finished products, including webs of material 3a, 3b wound in reels 4, such as for example polyethylene, nonwoven fabric, tissue, etc.

The webs of material 3a, Sb are continuously fed through the plant 1 along respective paths and are joined, shaped, conformed and cut, etc., in order to produce the abovementioned pull-up diapers 2.

In the schematic example illustrated in FIG. 1, the plant 1 comprises two reel holders 5 for the respective reels 4 of webs of material 3a, 3b and spools 7 for a plurality of elastic threads 8. A first web of material 3a and a second web of material 3b unwound from the respective reel holder 5 and the elastic threads 8 unwound from the spools 7 are fed along respective paths and directed towards a coupling device 9 defined by a pair of opposite and motorized coupling rollers 10.

The first web of material Sa and the second web of material 3b are for example nonwoven fabrics.

Figure 2:
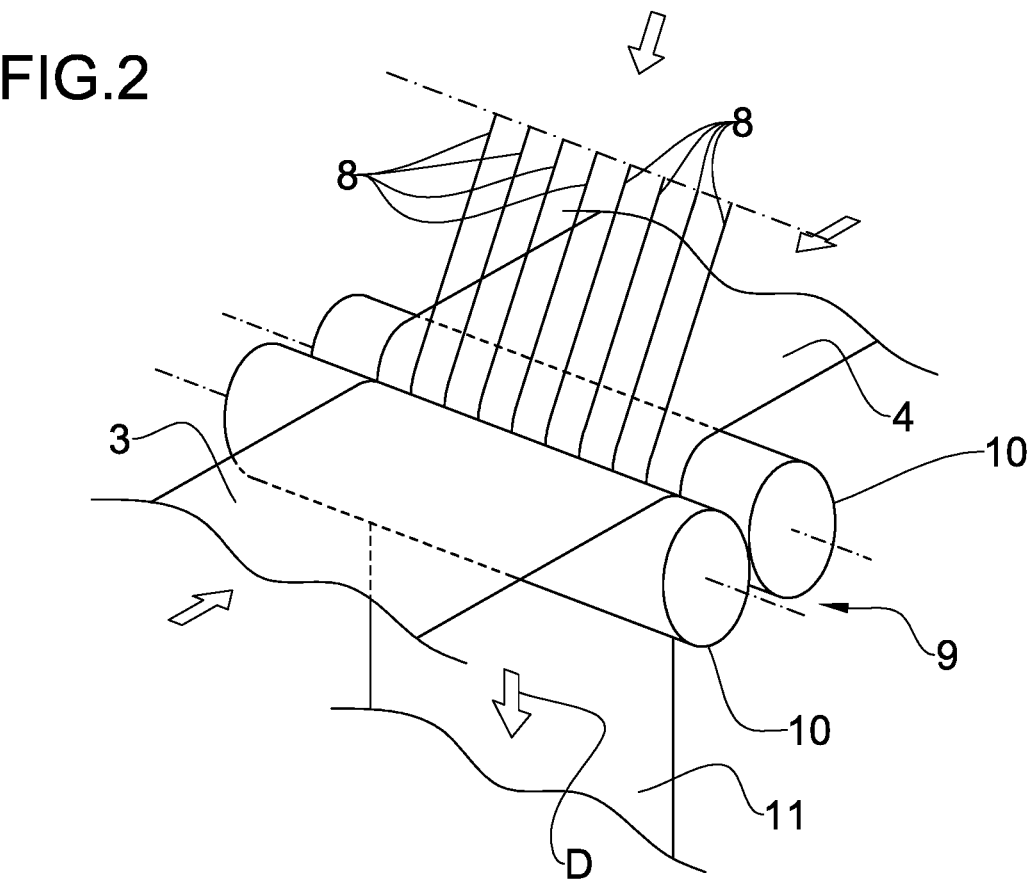
FIG. 2 schematically illustrates a device of the plant of FIG. 1.

The coupling device 9 is configured to longitudinally insert the plurality of elastic threads 8 between the first web of material 3a and the second web of material 3b and join the plurality of elastic threads 8 to the first web of material 3a and to the second web of material 3b. As illustrated in FIG. 2, the first web of material 3a and the second web of material 3b pass between radially peripheral surfaces of the two coupling rollers 10 and the elastic threads 8 move between the two coupling rollers 10 and between the first web of material 3a and the second web of material 3b. In the illustrated embodiment, the elastic threads S are parallel to each other and are distributed over the entire width of the webs of material 3a, 3b in order to have an elasticized weave which is as uniform as possible.

Upstream of the two coupling rollers 10, there is a hot glue dispenser, not illustrated, which provides for spraying the elastic threads 8 with the glue before they pass between the two coupling rollers 10 and between the first web of material 3a and the second web of material 3b. The two coupling rollers 10 compress the first web of material 3a and the second web of material 3b on the elastic threads 8, causing the joining thereof. Alternatively, it is possible to use other instruments for coupling the wires to the webs, e.g. an ultrasound welder. The two coupling rollers 10 make the glue deposited on the elastic threads 8 adhere to the two webs of material 3a, 3b, rendering them integral but provided with different tensions.

A control unit, not illustrated, is operatively connected to devices for feeding the first web of material Sa and the second web of material 3b, to devices for feeding the plurality of elastic threads 8 and to the coupling device 9 and is configured and/or programmed to adjust feeding speeds of the first web of material 3a, of the second web of material 3b and of the plurality of elastic threads 8, conferring suitable elongations/tensions to the webs 3a, 3b and to the elastic threads 8.

During joining, a first supply tension "T1" is conferred to the first web of material and to the second web of material and hence to the composite elastic web 11.

For example, the first and the second web of material 3a, 3b are inserted between the two coupling rollers 10 with a tension of about 2.5 kg per meter of width of the respective web, such that the first and the second web of material 3a, 3b are completely extended. The first and the second web of material 3a, 3b in this step have an elongation that is substantially zero (possibly of several millimeters per linear meter). The elastic threads 8 are inserted between the two coupling rollers 10 and between the two webs of material 3a, 3b with a high percentage elastic elongation (first percentage elastic elongation Δ1%), usually equal to the maximum percentage elastic elongation (before breakage) of said elastic threads 8. For example a 380 dTex thread is elongated 400%. Threads with different dTex can be used (e.g. 540 or 840 dTex) which are elongated with different percentages.

The coupling device 9 therefore forms a composite elastic web 11 which comprises the first web of material 3a, the second web of material 3b and the plurality of elastic threads 8 arranged longitudinally between the first web of material 3a and the second web of material 3b. At the time of coupling with the two webs of material 3a, 3b, the tension of the elastic threads 8 remains that set, e.g. 400%. The value of the elongation of the two webs of material 3a, 3b during the coupling with the elastic threads 8 remains that original, i.e. substantially zero.

The coupling device 9 therefore constitutes a unit for feeding the composite elastic web 11.

Downstream of the coupling device 9, the composite elastic web 11 is advanced along a path thereof and according to an advancing direction "D". The elastic threads 8 of the composite elastic web 11 would tend to contract and wrinkle the composite elastic web 11 up to making the elastic threads 8 return to their rest configuration, but due to the stretch rollers present in the plant 1, the tension can be adjusted, giving the composite elastic web 11 the possibility to be contracted or eliminating that possibility.

The plant 1 comprises a pair of motorized rollers 12 defining opposite motorized surfaces, configured to engage and advance the composite elastic web 11 along said path and according to the advancing direction "D".

Downstream of the pair of motorized rollers 12, a leg-opening unit 6 is situated, which is placed along the feeding path, operates downstream of the feeding unit and is configured for cutting out, in an intermediate portion of the composite elastic 1o web 11, openings 22 for the legs. The leg-opening unit 6 is of rotary type and comprises a roller 13a placed above and provided with a knife C and a counter-roller 13b or counter-knife place below.

The roller 13a and the counter-roller 13b have respective rotation axes that are parallel to each other and are arranged with cylindrical surfaces thereof facing each other. The roller 13a and the counter-roller 13b are placed in rotation by means of motors, for example servomotors controlled by machine PLC or directly by the transmission line of the machine by means of cardan joints and reducers.

The knife C is arranged on a cylindrical lateral surface of the roller 13a and is defined by a blade that is extended on the cylindrical lateral surface of the roller 13a according to a closed path that is suitably shaped (see FIG. 4) as a function of the shape of the openings 22 to be generated in the composite elastic web 11.

The blade projects from the cylindrical lateral surface of the roller 13a and is made on said roller 13a by means of removal of material from the cylindrical lateral surface itself, which is made of a very hard material, e.g. of K110 tempered steel under vacuum or of a material that is also very hard, like tungsten carbide. The roller 13a is constituted by said very hard material so to be able to preserve the cutting wire as long as possible.

The blade has a pointed form with an angle comprised for example between 50° and 120° and a cutting point of the blade has a width comprised for example between 0.01 mm and 0.025 mm.

Also the counter-roller 13b is made of hard material, for example of K110 steel hardened by means of heat treatment or made of tungsten carbide. The external surface of the counter-roller 13b is rendered smooth and ground in order to create a cutting surface that is as uniform as possible.

Depending on the dimensions of the composite elastic web 11 to be cut and on the dimensions of the diapers 2 to be made, the roller 13a can comprise multiple knives C that are equivalent to each other regarding shape and arranged in succession along a circumferential direction and with a predefined pitch on the cylindrical lateral surface of the roller 13a, so as to obtain openings 22 that are equivalent and equally spaced on the composite elastic web 11 to be cut.

In order to avoid prematurely wearing out the blade of the knife C, the weight of the roller 13a with the knife C is compensated for or canceled by springs that maintain the knife C lifted from the counter-roller 13b by several millimeters. In addition, pneumatic cylinders operatively coupled to the roller 13a allow metering, by means of a pressure regulator, a pressure exerted by the roller 13a and by the knife C on the counter-roller 13b, i.e. a cutting force exerted on the point of the blade.

The leg-opening unit 6 comprises a suction mouth 29 placed downstream (with respect to the direction for feeding the composite elastic web 11) of the roller 13a and of the counter-roller 13b and operatively connected to suction devices. The suction mouth 29 illustrated with continuous section in FIGS. 3 and 4 is placed below the composite elastic web 11 and is directed towards the counter-roller 13b.

The leg-opening unit 6 is configured for cutting out, in the intermediate portion of the composite elastic web 11, the openings 22 for the legs while the composite elastic web 11 passes and advances with continuity between the roller 13a and the counter-roller 13b. The counter-roller 13b, rotating in contact with the blade of the knife C, together with the knife C provides for cutting the material that is interposed, giving the shape of the blade to the composite elastic web.

The suction mouth 29 is configured for removing and moving away the portion of the composite elastic web 11 cut out by the knife C. The cut-out portion of the composite elastic web 11 is transported into a suitable container for processing trimming.

Figure 3:
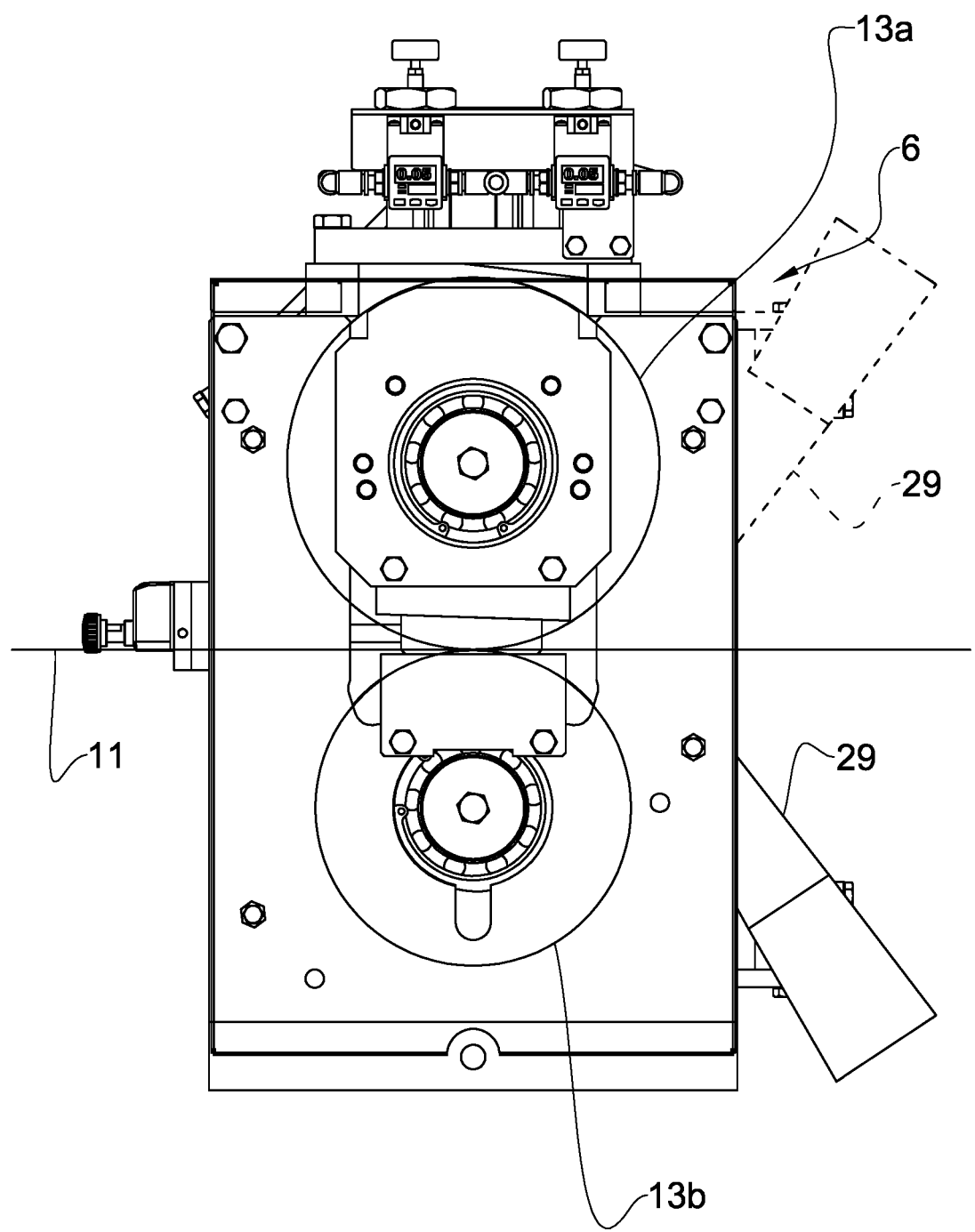
FIGS. 3 and 4 illustrate, in respective views, a different device of the plant of FIG. 1.
Figure 4:
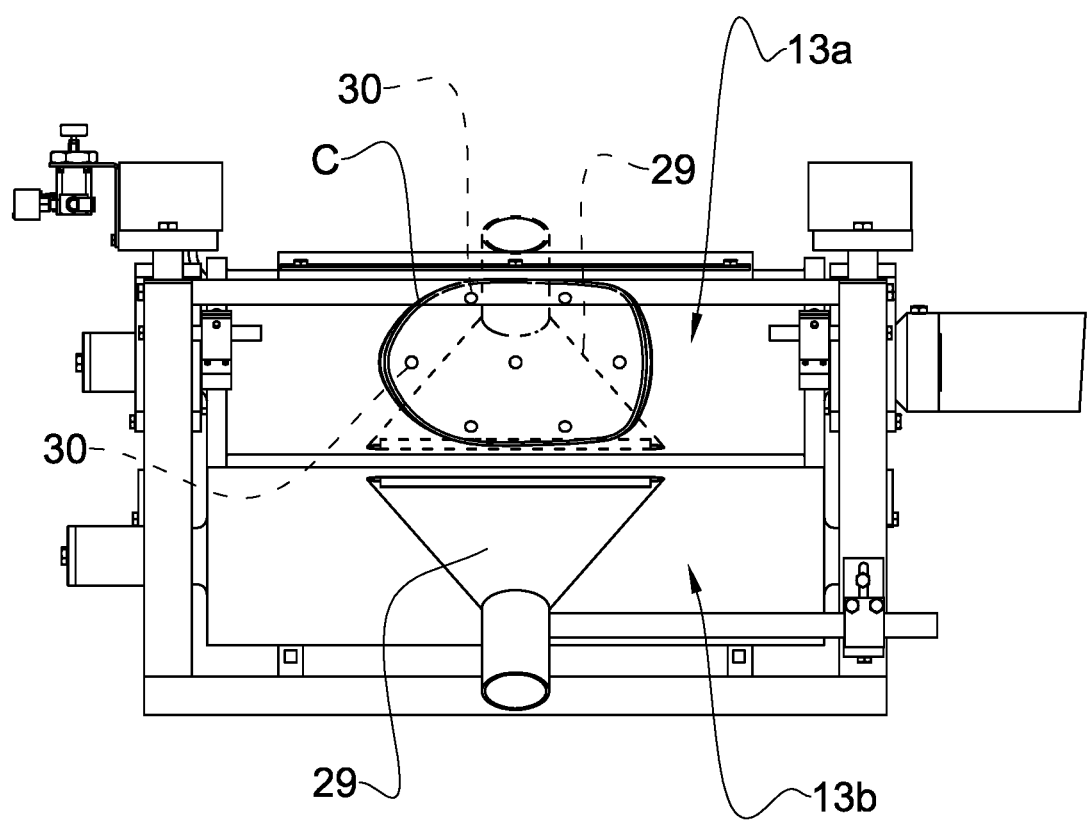

In an embodiment variant represented with dashed line in FIGS. 3 and 4, the suction mouth 29 is placed above the composite elastic web 11 and faces the roller 13a. The roller 13a also has holes 30 arranged on the external cylindrical surface and within an area delimited by the blade of the knife C (FIG. 4). The holes 30 are in fluid communication with suction and blowing devices and are configured for retaining, on the roller 13a, the portion of the composite elastic web 11 just cut out by the knife C and releasing it towards the respective suction mouth 29.

Both rollers 13a, 13b are supported by precision bearings, so to rotate perfectly concentric and obtain a perfect cutting. The knife C always rotates in phase with the web to be cut, so as to obtain a cutting repeatability and constant relative positioning with the diapers 2 being manufactured.

An applicator 14 operates downstream of the leg-opening unit 6 and is configured for applying, in succession on the composite elastic web 11, a plurality of absorbing inserts 15 while the composite elastic web 11 advances along the path and according to the advancing direction "D". Each absorbing insert 15 comprises, for example, an impermeable layer, a permeable layer and ground cellulose pulp mixed with super-absorbent powder arranged between the impermeable layer and the permeable layer.

The applicator 14 comprises a rotatable wheel 16 provided with a peripheral surface that constitutes a transport surface 17 for the absorbing inserts 15. The rotatable wheel 16 for example comprises suction devices, not illustrated, and operatively active on the peripheral surface, in order to retain the absorbing inserts 15, transport them and release them one at a time on the composite elastic web 11.

On one side of the rotatable wheel 16 (on the left of FIG. 1), a conveyor 18 is situated which provides for feeding in succession the absorbing inserts 15, manufactured in dedicated section of the plant 1, up to the rotatable wheel 16 and to release them on the transport surface 17. On an opposite side of the rotatable wheel 16 (on the right of FIG. 1), a conveyor belt 19 is situated which has a movable surface facing and close to the transport surface 17 at an application zone 20 of the applicator 14.

The applicator 14 also comprises a dispenser 21 of hot glue, e.g. of spray type, which is operatively active at the application zone 20 or immediately upstream of the same, in order to dispense the hot glue on the composite elastic web 11 and/or on each absorbing insert 15 before the absorbing insert 15 is brought by the rotatable wheel 16 against the composite elastic web 11.

The control unit is operatively connected to the coupling rollers 10 as well as to the pair of motorized rollers 12, to the rollers 13a, 13b of the leg-opening unit 6, to the rotatable wheel 16 and to the conveyor belt 19 and is configured for controlling/adjusting the speeds of such components.

The control unit is configured and/or programmed for conferring, to the two coupling rollers 10 and to the first pair of motorized rollers 12, linear peripheral speeds such to reduce the tension and the maximum percentage elastic elongation which the elastic threads 8 have (first percentage elastic elongation Δ1%) as soon as the composite elastic web 11 exits from the two coupling rollers 10.

In particular, the control unit is configured and/or programmed for conferring, to the pair of motorized rollers 12, linear peripheral speeds such to confer to the composite elastic web 11, exiting from the pair of motorized rollers 12, a reduced tension "T2" less than the first supply tension "T1" and such that the elastic threads 8 are allowed to partially contract.

In other words, one proceeds by passing the composite elastic web 11 through the pair of motorized rollers 12 which have a peripheral speed lower than the peripheral speed of the coupling rollers 10.

In this manner, the elastic threads 8 under tension inside the composite elastic web 11, partly freed from the tension for the frontal pulling, are retracted and provide for absorbing the speed difference between the pair of motorized rollers 12 and the coupling rollers 10, thus forming an elasticized composite material that from a more extensive size (maximum nominal elongation) reaches a smaller size (smaller elongation).

For example, the second tension is equal to 0.6 kg for 100 mm of width of elastic front, i.e. of the elasticized part of the composite elastic web 11. The elastic threads 8 take on a second percentage elastic elongation Δ2% less than the first percentage elastic elongation Δ1%.

For such purpose, a first linear speed "V1" of the coupling rollers 10 will be greater than a second linear speed "V2" of the pair of motorized rollers 12. For example, the second percentage elastic elongation Δ2% is about 240% and a ratio between the second percentage elastic elongation Δ2% and the first percentage elastic elongation Δ1% is equal to 0.6. In other words, the percentage elastic elongation is reduced by 40%. Also the first web of material 3a and the second web of material 3b are partially contracted following the elastics 8. The two webs of material 3a, 3b are integral with the elastic threads 8 and are not opposed to the contraction.

The control unit is configured and/or programmed for giving to the roller 13a and to the counter-roller 13b of the leg-opening unit 6 peripheral speeds equal to the second linear speed "V2". The composite elastic web 11 at this point moves between roller 13a and counter-roller 13b which provide to cut out the openings 22 for the legs.

The portions of the composite elastic web cut out by the knife C comprise parts of the two webs of material 3a, 3b and sections of the elastics 8 which are removed from a central band of the elastic element defined by the elastics 8 themselves. This operation therefore substantially cancels the percentage elastic elongation at the intermediate portion of the composite elastic web 11.

On the other hand, the elastic threads arranged in the two opposite lateral longitudinal portions of the composite elastic web 11, i.e. at the two sides of the intermediate portion, remain intact and with a certain elongation percentage, e.g. substantially equal to the second percentage elastic elongation.

Figure 5:
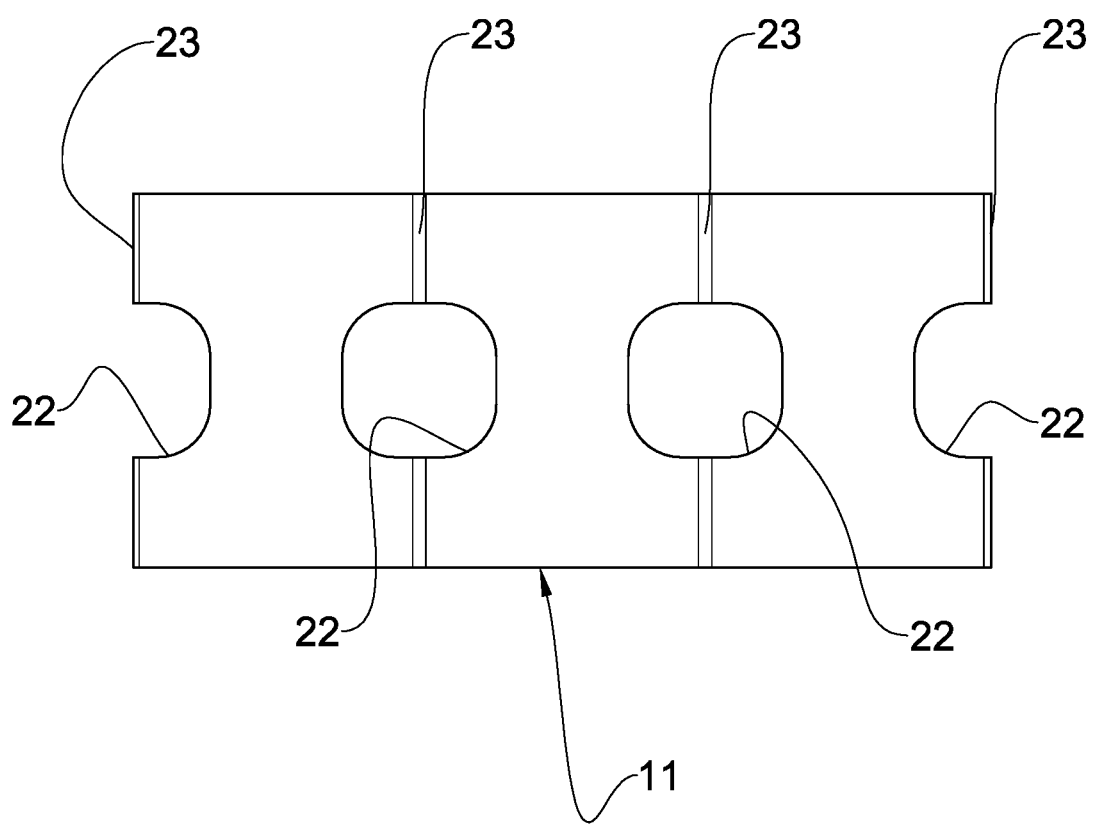

The composite elastic web 11 provided with openings 22 for the legs is illustrated in FIG. 5.

In accordance with the method of the present invention, the control unit is configured and/or programmed for conferring to the rotatable wheel 16 of the applicator 14 and to the conveyor belt 19 peripheral speeds such that the composite elastic web 11 is maintained under tension with said second tension or application tension "T2". In this manner, the elastic threads 8 arranged in the two opposite lateral longitudinal portions of the composite elastic web 11 are maintained elongated with the second percentage elastic elongation Δ2% while, as specified above, the percentage elastic elongation of the elastic threads 8 placed at the intermediate portion of the composite elastic web 11, i.e. between the openings 22 for the legs, is substantially zero. The absorbing inserts 15 are then applied and glued on the intermediate portion and between the openings 22 for the legs, i.e. in the zones with the elastic threads 8 at substantially zero elongation. A width "W" of the central band which corresponds to a maximum width of each opening 22 for the legs is less than or substantially equal to a length "L1" of an absorbing insert 15. For example, the width "W" of the central band or maximum width of each opening 22 for the legs is about 70% of the length "L1" of an absorbing insert 15. In addition, such width "W" of the central band is about 45% of a width "L2" of the composite elastic web 11. For example, the width "L2" of the composite elastic web 11 is comprised between about 650 mm and about 1000 mm depending on the cut; the width "W" of the central band or maximum width of each opening 22 for the legs is comprised between about 300 mm and about 450 mm depending on the cut; the length "L1" of an absorbing insert 15 is comprised between about 450 mm and about 650 mm depending on the cut.

The composite elastic web 11 provided with absorbing inserts 15 that exit from the applicator 14 and is transported on the conveyor belt 19 downstream of said applicator 14 is illustrated in FIG. 6.

An intermediate portion of the composite elastic web 11 corresponds to crotches of the pull-up diapers 2, each provided with the absorbing insert 15, and the two opposite lateral longitudinal portions of the composite elastic web 11 correspond to the waistbands of the pull-up diapers 2. The composite elastic web 11 defines a series of precursors of pull-up diapers, in which transverse separation zones 23 separate one precursor from the next.

In the non-limiting example illustrated in the enclosed FIGS. 5-8, the absorbing inserts 15 and the openings 22 for the legs were represented symmetric with respect to a middle line of the composite elastic web 11 but the position and the form of said absorbing inserts 15 and/or openings 22 for the legs can also be asymmetric with respect to said middle line.

At one end 24 of the conveyor belt 19, a folding device 25 is situated, which is configured for longitudinally folding the composite elastic web 11 and bringing opposite flaps of each transverse separation zone 23 close to each other, for example as illustrated in FIG. 7 in which the composite elastic web 11 is folded longitudinally in two. The folding is executed while the composite elastic web 11 continues to advance along the path thereof.

Once folded, the composite elastic web 11 is transported up to a joining device 26 and to a cutting device 27 placed downstream of the folding device 25 and configured for joining together the opposite flaps of each transverse separation zone 23 and for cutting the composite elastic web 11 at cutting lines 28 (FIG. 7) situated in the transverse separation zones 23 and obtaining the single pull-up diapers 2 (FIG. 8). Downstream of the formation of the openings 22 for the legs and until before the cutting in the single pull-up diapers 2, the composite elastic web 11 is maintained, for example, at the second tension or application tension "T2".

The transverse separation zones 23 are joined, for example by means of heat welding or ultrasound welding, so as to form such bands, and then such bands are cut at the cutting middle lines 28 (indicated in FIG. 7). When the cutting is executed, the tension of the conveyor belt 11 is completely released and each pull-up diaper 2 is contracted due to the contraction of the elastic threads 11 which tend to be brought to zero elongation. One of the pull-up diapers 2 obtained is illustrated in FIG. 8.

Since the absorbing insert 15 is applied to the composite elastic web 11 at the central band of the elastic element, where the percentage elastic elongation of the elastic threads 8 is substantially zero, such absorbing insert 15 of each single pull-up diaper 2, once the tension is completely released, remains substantially flat or does not form substantial folds or wrinkles.

Such effect is also ensured by the fact that the absorbing inserts 15 are applied to the composite elastic web 11 once the tension of the composite elastic web 11 is partly released and hence while the elastic threads 8 of the two opposite lateral longitudinal portions possess a reduced percentage elastic elongation. Hence, also the ends of each absorbing insert 15 that lie at the two opposite lateral longitudinal portions, once the tension is completely released, remain substantially flat or do not form substantial folds or wrinkles or they only form weak undulations that are not annoying and in any case do not compromise the operation of the diaper 2 itself.

In embodiment variants, not illustrated, the tension of the composite elastic web 11 is not reduced but is constant along the entire feeding path. The tension can be such to always maintain the elastic threads 8 at the maximum percentage elastic elongation. In this case, the elimination of the folds at the absorbing inserts 15 is only due to the execution of the openings 22 for the legs before the application of said absorbing inserts 15. The tension can also be such to always maintain the elastic threads 8 at an elongation lower than the maximum percentage elastic elongation, e.g. at the second percentage elastic elongation Δ2% described above.

In embodiment variants, instead of producing the composite elastic web 11 in line by means of the coupling device 9, the composite elastic web 11 is previously produced in a seat and/or with a different apparatus/device and then wound in a reel on a reel holder. With reference to FIG. 1, in place of the coupling device 9, a reel holder is therefore present with the composite elastic web 11 wound in a reel and the first pair of motorized rollers 12 is therefore situated just downstream of the reel holder. The composite elastic web 11 is wound in a reel with its elastic threads 8 with the maximum percentage elastic elongation or with a reduced elongation.

According to embodiment variants, not illustrated in detail, the elastic threads 8 are distributed only on part of the width of the composite elastic web 11.

According to other embodiments, not illustrated in detail, in place of the elastic threads 8 interposed between the two webs of material 3a, 3b, the composite elastic web 11 comprises one or more elasticized layers of fabric or nonwoven fabric.

ELEMENTS 1 plant
2 pull-up diapers
3a, 3b webs of material
4 reels
5 reel holder
6 leg-opening unit
7 spools
8 elastic threads
9 coupling device
10 pair of coupling rollers
11 elastic web 12 pair of motorized rollers
13a, 13b roller and counter-roller
14 applicator
15 absorbing inserts
16 rotatable wheel
17 transport surface
18 conveyor
19 conveyor belt
20 application zone
21 dispenser of hot glue
22 openings for the legs
23 separation zones
24 end of the conveyor belt
25 folding device
26 joining device
27 cutting device
28 cutting lines
29 suction mouth
30 holes
C knife
D advancing direction
Δ1% first percentage elastic elongation
Δ2% second percentage elastic elongation
T1 first tension
T2 second tension or application tension
V1 first linear speed
V2 second linear speed
W width of the central band
L1 length of an insert
L2 width of the composite elastic web

The invention claimed is:

1. A process for producing pull-up diapers, comprising:
producing a composite elastic web comprising at least one web of material and at least one elastic element longitudinally coupled to the at least one web of material;
feeding the composite elastic web along a feeding path and according to a feeding direction, by giving the composite elastic web at least one supply tension such that the at least one elastic element has at least one corresponding supply percentage elastic elongation;
cutting out openings for the legs in an intermediate portion of the composite elastic web while the composite elastic web advances;
applying absorbing inserts on the intermediate portion of the composite elastic web and between successive openings for the previously cut-out legs while the composite elastic web advances, so as to define a series of precursors of pull-up diapers, wherein the intermediate portion of the composite elastic web corresponds to crotches of the pull-up diapers, each provided with the absorbing insert, and two opposite lateral longitudinal portions of the composite elastic web correspond to the waistbands of the pull-up diapers and wherein transverse separation zones separate one precursor from the next;
longitudinally folding the composite elastic web so as to bring together opposite flaps of each transverse separation zone and joining together the opposite flaps; and
cutting the composite elastic web at the transverse separation zones in order to obtain the single pull-up diapers; wherein
cutting out the openings for the legs involves substantially canceling the supply percentage elastic elongation in the central band of the elastic element corresponding to the intermediate portion of the composite elastic web;
the composite elastic web has a maximum nominal elongation corresponding to a nominal width of the pull-up diapers to be produced; wherein, when the composite elastic web is at its maximum nominal elongation, the at least one web of material is completely extended and the at least one elastic element has a first percentage elastic elongation;
before applying the absorbing inserts, a reduced tension is provided to the composite elastic web, such that the composite elastic web has an elongation less than its maximum nominal elongation and the at least one elastic element has a second percentage elastic elongation less than the first percentage elastic elongation;
the reduced tension is conferred before or after cutting out the openings for the legs; and
after having cut out the openings for the legs, the second percentage elastic elongation belongs to the two opposite lateral longitudinal portions of the composite elastic web.

2. The process according to claim 1, wherein the at least one elastic element is extended substantially over the entire width of the composite elastic web.

3. The process according to claim 1, wherein a width of the central band and/or a maximum width of each opening for the legs is less than or substantially equal to a length of an absorbing insert.

4. The process according to claim 1, wherein the composite elastic web comprises a first web of material, a second web of material and the at least one elastic element arranged longitudinally between the first web of material and the second web of material.

5. The process according to claim 4, wherein
the composite elastic web comprises a plurality of elastic threads arranged longitudinally between the first web of material and the second web of material;
the at least one elastic element of the composite elastic web comprises the or is defined by the plurality of elastic threads; and
cutting out the openings for the legs involves cutting the elastic threads arranged in the central band, leaving intact the elastic threads arranged in the two opposite lateral longitudinal portions of the composite elastic web.

6. The process according to claim 5, wherein the elastic threads are arranged over the entire width of the first web of material and of the second web of material.

7. The process according to claim 5, wherein
producing the composite elastic web comprises:
feeding the first web of material and the second web of material along respective paths;
feeding the plurality of elastic threads along a respective path;
inserting the plurality of elastic threads between the first web of material and the second web of material; and
joining the plurality of elastic threads to the first web of material and to the second web of material while the first web of material, the second web of material and the plurality of elastic threads advance along a common path, in order to form the composite elastic web.

8. The process according to claim 7, wherein, during joining, the elastic threads are given the first percentage elastic elongation and the first web of material and the second web of material are completely extended.

9. The process according to claim 1, wherein a ratio between the second percentage elastic elongation and the first percentage elastic elongation is less than 0.99 and greater than 0.3.

10. The process according to claim 1, wherein a ratio between the second percentage elastic elongation and the first percentage elastic elongation is less than 0.7 and greater than 0.5.

11. The process according to claim 1, wherein the first percentage elastic elongation is comprised between 200% and 600% of a rest length.

12. The process according to claim 1, wherein the second percentage elastic elongation is comprised between 100% and 300% of a rest length.

13. The process according to claim 1, wherein the reduced tension is comprised between 0.2 Kg and 1 Kg per 100 mm of width of an elasticized part of the composite elastic web.

* * * * *